United States Patent [19]
Wellinger et al.

[11] Patent Number: 6,025,135
[45] Date of Patent: Feb. 15, 2000

[54] TELOMERE MAINTENANCE ASSAYS

[75] Inventors: Raymund J. Wellinger, Sherbrooke, Canada; Virginia A. Zakian, Princeton, N.J.

[73] Assignees: The Trustees of Princeton University, Princeton, N.J.; Universite de Sherbrooke, Quebec, Canada

[21] Appl. No.: 08/850,711

[22] Filed: May 2, 1997

Related U.S. Application Data

[60] Provisional application No. 60/016,718, May 2, 1996.
[51] Int. Cl.$^7$ ............... C12Q 1/68; C12Q 1/34; C12N 9/16
[52] U.S. Cl. ............... 435/6; 435/4; 435/194; 435/196; 435/254.2; 435/325; 536/23.1
[58] Field of Search .................. 435/4, 6, 196, 435/194, 325, 254.2; 536/23.1

[56] References Cited

U.S. PATENT DOCUMENTS

| | | | |
|---|---|---|---|
| 5,002,875 | 3/1991 | Lacks et al. | 435/69.1 |
| 5,145,776 | 9/1992 | Tabor et al. | 435/91 |
| 5,489,508 | 2/1996 | West et al. | 435/6 |

OTHER PUBLICATIONS

Wellinger et al. Saccharomyces telomeres acquire single–strand TG 1–3 tails late in S phase. Cell vol. 72 pp. 51–60, 1993.

Kerr et al., "Gene 6 exonuclease of Bacteriophage T7," *J. of Biological Chemistry*, Jan. 10, 1972, vol. 247, No. 1, pp. 311–318, especially pp. 312–313.

*Primary Examiner*—John S. Brusca
*Attorney, Agent, or Firm*—Townsend and Townsend and Crew LLP

[57] ABSTRACT

The strand of telomeric DNA that runs 5' to 3' towards a chromosome end is typically G-rich. Due to the properties of conventional DNA polymerases, telomerase-generated tails of this G-rich strand are expected on only one end of individual linear DNA molecules. In Saccharomyces, $TG_{1-3}$ tails are detected on chromosome and linear plasmid telomeres late in S-phase. Moreover, the telomeres of linear plasmids can interact when the $TG_{1-3}$ tails are present. Molecules were generated in vitro that mimic the structures predicted for telomere replication intermediates. These in vitro generated molecules formed telomere—telomere interactions similar to those on molecules isolated from yeast but only if both ends that interacted had a $TG_{1-3}$ tail. Moreover, $TG_{1-3}$ tails were generated in vivo in cells lacking telomerase. These data suggest a new step in telomere maintenance cell cycle regulated degradation of the $C_{1-3}A$ strand which can generate a potential substrate for telomerase and telomere binding proteins at every telomere.

17 Claims, 9 Drawing Sheets

SEQUENCE LISTING (1) GENERAL INFORMATION:

(iii) NUMBER OF SEQUENCES: 1

(2) INFORMATION FOR SEQ ID NO:1:

(i) SEQUENCE CHARACTERISTICS:
      (A) LENGTH: 15 base pairs
      (B) TYPE: nucleic acid
      (C) STRANDEDNESS: single
      (D) TOPOLOGY: linear (ii) MOLECULE TYPE: DNA (xi) SEQUENCE DESCRIPTION: SEQ ID NO:1:

GTGTGGTGTG GGTAC                      15

TELOMERE MAINTENANCE ASSAYS

This application claims the benefit of U.S. Provisional application Ser. No. 60/016,718, filed May 5, 1996, the disclosure of which is incorporated by reference.

BACKGROUND OF THE INVENTION

This invention relates to methods of assaying for 5' to 3' exonuclease activity.

Telomeric DNA of virtually all organisms is composed of short direct repeats with clustering of G residues on the strand that forms the 3' end of the chromosome (Zakian, 1995). In some protozoans, the precise structure of the very ends of the macronuclear DNA molecules is a 10–16 base overhang of the G-rich strand (Klobutcher et al., 1981; Pluta et al., 1982; Henderson and Blackburn, 1989). In Oxytricha and related ciliates, there are proteins that bind specifically to this G-rich tail (Gottschling and Zakian, 1986; Price, 1990). In vitro, these proteins protect telomeric DNA from degradation (Gottschling and Zakian, 1986). Although it is not yet known if short, G-rich overhangs are a general feature of telomeres, genetic (Wiley and Zakian, 1995) and biochemical (Cardenas et al., 1993) studies suggest that diverse organisms have terminus-limited telomere binding proteins similar to those described in Oxytricha. These data suggest that telomeres in many organisms will be found to have short, constitutive G-tails that serve as substrates for essential telomere binding proteins.

Telomeres are essential for chromosome integrity: they protect chromosome ends from random fusion events and degradation (McClintock, 1939, 1941; Sandell and Zakian, 1993) and they ensure the complete replication of the chromosome (Watson, 1972; Olovnikov, 1973). Conventional DNA polymerases require a primer and can synthesize DNA only in the 5' to 3' direction. This enzymatic machinery is expected to leave 8–12 base gaps at the 5' ends of the newly synthesized strands after removal of the last RNA primer (Newlon, 1988). A priori, this gap is expected on only half of the telomeres, the ones on which the newly synthesized strand is made by lagging strand synthesis (FIG. 1A). Telomerase is a ribonucleoprotein that uses a sequence within its RNA as template for the addition of telomeric repeats (reviewed in Greider, 1995). This enzyme can extend the short 3' overhangs left after primer removal to generate overhangs of telomeric G-strand DNA. On the other half of the telomeres, leading strand synthesis is expected to leave a blunt end (FIG. 1A). If telomere binding proteins require a short overhang of the G-rich strand for binding, the blunt end must somehow be processed to generate such a structure (Lingner et al., 1995 and see below). Since in vitro, a blunt end does not serve as a substrate for telomerase, additional, so far unknown activities must be invoked for this processing (Lingner, et al., 1995).

In *Saccharomyces cerevisiae*, telomeres consist of ~300 bp of $C_{1-3}A/TG_{1-3}$ sequences that are necessary and sufficient for all essential functions of telomeres (see for example Wellinger and Zakian, 1989; Sandell and Zakian, 1993). The Applicant showed previously that at the end of S-phase a >30 base long overhang of the G-rich strand (hereafter referred to as $TG_{1-3}$ tails) occurs on yeast telomeres (Wellinger et al., 1992, 1993b, c). At other points in the cell cycle, overhangs are not detected although overhangs ≦30 bases were not detectable in these studies. Short linear plasmids also acquire $TG_{1-3}$ tails immediately after replication of telomeric DNA by conventional replication (Wellinger et al., 1993c). In addition, these linear plasmids form telomere—telomere associations that are dependent on the presence of the $TG_{1-3}$ tails (Wellinger et al., 1993a, c).

Oligonucleotides of single stranded G-rich telomeric DNA from ciliates, vertebrates and yeast form alternative DNA structures in vitro that depend on non-canonical base pairing of the guanines (for reviews, see Sundquist, 1990, 1993). The best described structures are G-quartets, four stranded parallel or anti-parallel helices in which four guanines are in a planar alignment to each other and in which every G has two hydrogen bonds to each of two neighboring Gs (Gellert et al., 1962; Sen and Gilbert, 1988; Sundquist and Klug, 1989; Williamson et al., 1989; Kang et al., 1992; Smith and Feigon, 1992). The formation of G-quartets by intermolecular interactions is slow and requires specific cations for stabilization of the product (Sundquist and Klug, 1989; Williamson et al., 1989; Sen and Gilbert, 1990; Hardin et al., 1991; Scaria et al., 1992). In addition, a guanine may simply base pair with another guanine to form a G:G base pair (Hobza and Sandorfy, 1987; Sundquist, 1990; Gualberto et al., 1992). One possible G:G base pairing configuration has been calculated to be second only to a G:C base pair in stability (Hobza and Sandorfy, 1987). Alternatively, a single stranded G-rich DNA strand may associate with double-stranded G:C rich DNA to form a triple helix via G·G:C pairing (Beal and Dervan, 1991; Voloshin et al., 1992; Cheng and Van Dyke, 1993; Gilson et al., 1994). At least in vitro, this association requires $Mg^{++}$ ions or spermine in the reaction mixture (Kohwi and Kohwi-Shigematsu, 1988; Beal and Dervan, 1991).

At least two alternatives could explain the end-to-end interactions observed with in vivo generated short linear plasmids containing $TG_{1-3}$ tails (Wellinger et al., 1993c). As outlined above, the individual daughter molecules left after conventional replication and $TG_{1-3}$ tail formation could have a blunt end on one telomere and a $TG_{1-3}$ tail on the other (FIG. 1A). In this case, the $TG_{1-3}$ tail from one end could associate with the double-stranded $C_{1-3}A/TG_{1-3}$ repeats on the other by forming a triple helix. Alternatively, if there is a mechanism to generate a $TG_{1-3}$ tail on the end replicated by leading strand synthesis, both ends of individual daughter molecules could have $TG_{1-3}$ tails (FIG. 1B). These $TG_{1-3}$ tails could then associate via G-quartet structures or G:G base pairing.

SUMMARY OF THE INVENTION

Using an in vitro system that generates molecules that mimic both possible replication intermediates, the Applicant demonstrated telomere—telomere interactions analogous to those observed with molecules synthesized in vivo. The end-to-end associations on in vitro generated molecules occurred rapidly and did not require high monovalent cation concentrations or $Mg^{++}$ in the reaction mixtures. Most importantly, these telomere—telomere interactions on in vitro generated molecules occurred only if both interacting ends had a $TG_{1-3}$ tail. When the in vivo generated molecules were heated to temperatures that dissociated the telomere—telomere interactions, these molecules reformed telomere—telomere interactions in vitro. Therefore, the in vivo generated molecules must have $TG_{1-3}$ tails at both ends. Moreover, $TG_{1-3}$ tails and telomere—telomere interactions were detected in strains lacking telomerase. These data suggest that there are telomerase-independent mechanisms that can generate a $TG_{1-3}$ tail on the ends replicated by both leading and lagging strand synthesis in a cell cycle regulated manner.

In one aspect, the invention provides a method for detecting 5'→3' exonuclease activity in a sample comprising the steps of: contacting the sample with a substrate linear double-stranded nucleic acid molecule wherein at least one end of such molecule does not have a 3' overhang; and determining whether a resulting linear nucleic acid molecule has 3' overhangs at both ends, whereby the presence of 3' overhangs at both ends of the resulting nucleic acid molecule indicates the presence of 5'→3' exonuclease activity in the sample.

In a preferred aspect, the sample comprises a cell transfected with the linear nucleic acid molecule, wherein the cell is preferably a yeast. More preferably, the cell lacks telomerase activity.

In another preferred aspect the 3' overhang on the first end comprises $TG_{1-3}$ repeats. The exonuclease is preferably FEN-1 or RAD27, or a mammalian, more preferably human, homologue thereof. The exonuclease is preferably involved in telomere maintenance.

In one aspect, the determination of whether a resulting nucleic acid molecule has 3' overhangs at both ends is based on whether the resulting nucleic acid molecule can undergo end-to-end interactions. Preferably, end-to-end interactions are assessed by determining if the resulting molecule circularizes or forms linear concatenations of at least three linear nucleic acid molecules. The determination of whether both ends of the linear nucleic acid molecule have 3' overhangs based on whether the molecule forms linear concatenations preferably comprises determining the length of the 3' overhangs in the linear nucleic acid molecule.

In another aspect, the invention provides a method for determining whether a compound modulates the activity of a 5'→3' exonuclease in a sample, wherein the sample contains the compound and a known quantity of 5'→3' exonuclease, and the method comprises the steps of:
  contacting the sample with a substrate linear double-stranded nucleic acid molecule wherein at least one end of such molecule does not have a 3' overhang;
  determining the amount of 5'→3' exonuclease activity in the sample after contact with the compound; and
  comparing the amount of 5'→3' exonuclease activity in the sample with a standard activity for the same quantity of the exonuclease, whereby a difference between the amount of activity in the sample and the standard activity indicates that the compound modulates the activity of the 5'→3' exonuclease.

In another aspect, the invention provides a method for determining whether a compound modulates the activity of an enzyme which regulate 5'→3' exonuclease, wherein the sample contains a known quantity of 5'→3' exonuclease and the enzyme, and the method comprises the steps of:
  contacting the sample with a substrate linear double-stranded nucleic acid molecule wherein at least one end of such molecule does not have a 3' overhang;
  determining the amount of 5'→3' exonuclease activity in the sample after contact with the compound; and comparing the amount of 5'→3' exonuclease activity in the sample with a standard activity for the same quantity of the exonuclease; and
  comparing the amount of 5'→3' exonuclease activity in the sample before and after contact with the compound, whereby a difference between the amount of activity in the sample before and after contact with the compound, beyond that which can be attributed to the effect of the compound directly on the exonuclease, indicates that the compound modulates the activity of the enzyme.

Preferably, the enzyme is protein kinase.

molecular size standards. The junction fragments are indicated by arrows. On the right is the autoradiogram of the same blot after rehybridization with probe B (see FIG. 2B). B) Thermal stability of end-to-end interactions of in vitro produced molecules. The DNA was derived from pYLPVΔs and had a G-rich telomeric extension on one end (A end) and a block of double-stranded telomeric repeats on the other (B end). The DNA was restricted with SspI and SalI as was done in the experiment described in FIG. 4A and incubated for 10 min at the indicated temperatures prior to loading onto an agarose gel. The DNA was then blotted onto a nylon membrane and probed with end-specific probes for both ends of the plasmid (left: probe A: right: probe B, see FIG. 2B). The terminal restriction fragment of the A-end is expected to be 1.3 kb and the terminal fragment of the B-end is 0.95 kb as in FIG. 4A. The arrow indicates the 2.6 kb fragment that hybridizes with probe A only. M: molecular size standards.

Figure 5A:
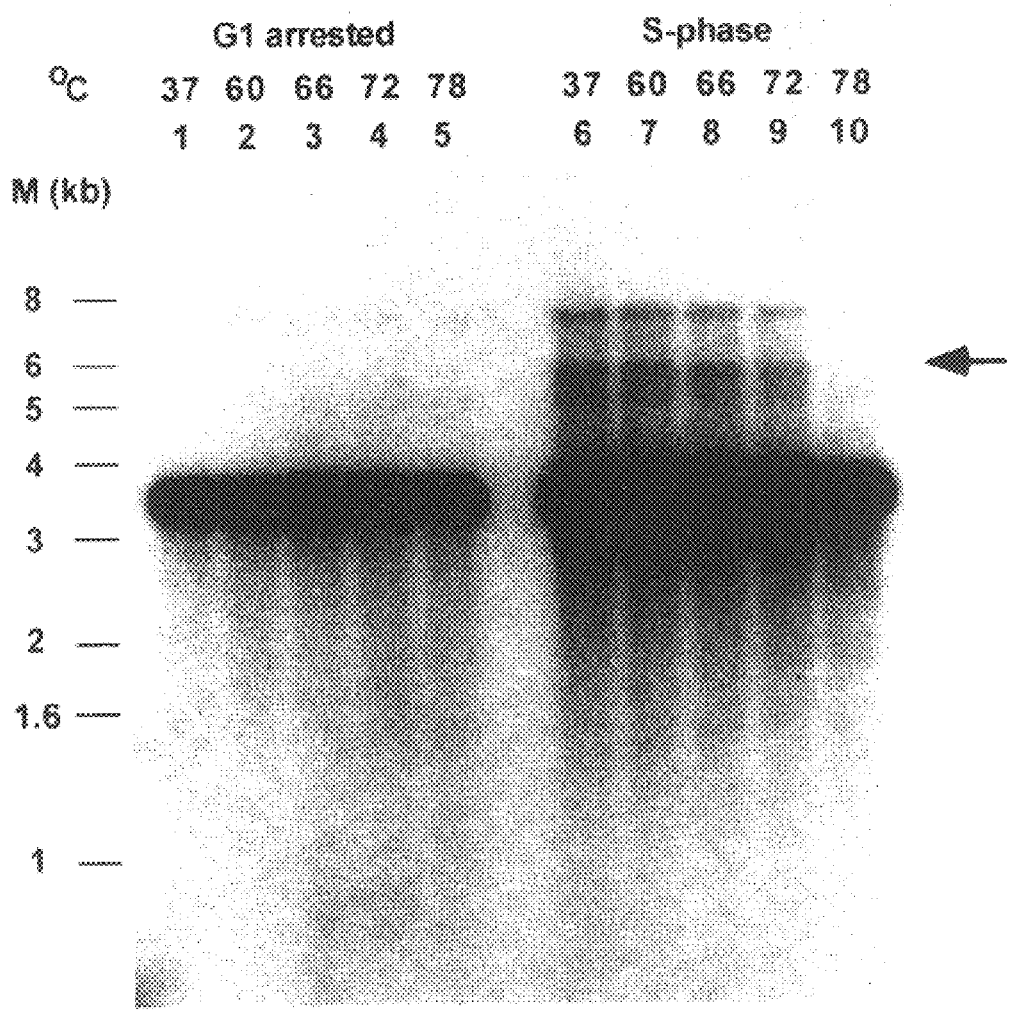
Figure 5B:
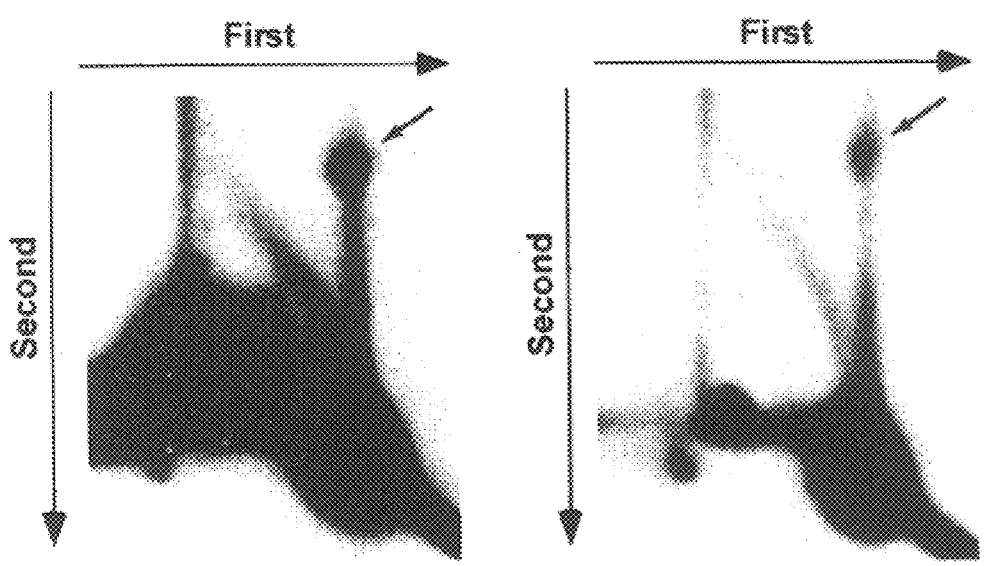

FIGS. 5A–5B. End-to-end interactions of the linear plasmid YLpFAT10 isolated from yeast cells. A) DNA of cells arrested in G1 (G1 arrested) or DNA of cells in late S-phase (S-phase) containing YLpFAT10 was first digested with NsiI and then incubated for 10 min at the indicated temperatures. This DNA was then analyzed by Southern blotting and probing with a pvz1 probe. This probe will detect a terminal fragment of ~3.5 kb (main band, see FIG. 2A). The arrow indicates the junction fragment. Note that the bands above and below the junction fragment correspond to partial digests of linear YLpFAT10 molecules and are visible in all lanes. M: molecular size standards. B) DNA of cells in late S-phase and containing YLpFAT10 was analyzed using two-dimensional agarose gels as described above and the Southern blots were hybridized with a pVZ1 probe. Left: control; DNA was loaded without heat treatment. Right: the DNA was incubated for 10 min at 78° C., cooled to room temperature and then loaded onto the gel. The arc above the diagonal of double-stranded DNA molecules corresponds to the conventional replication intermediates of YLpFAT10. The arrows point to CFP. Note that there was somewhat more DNA loaded on the gel on the left. After quantitation of the gels, the actual fractions of CFP/total DNA were about the same for the two gels (data not shown).

Figure 6A:
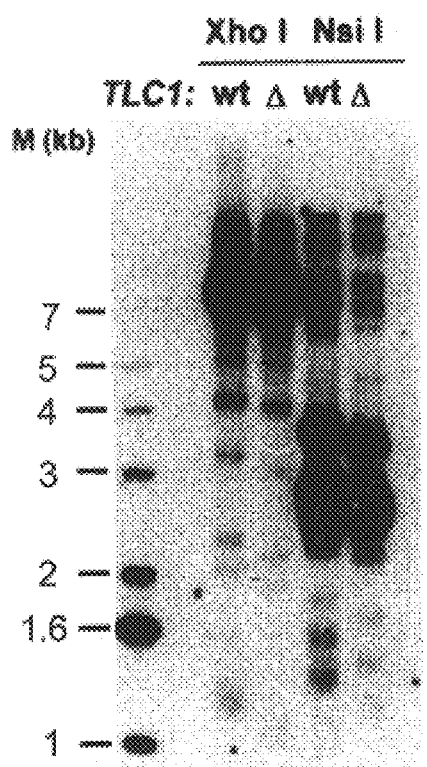
Figure 6B:
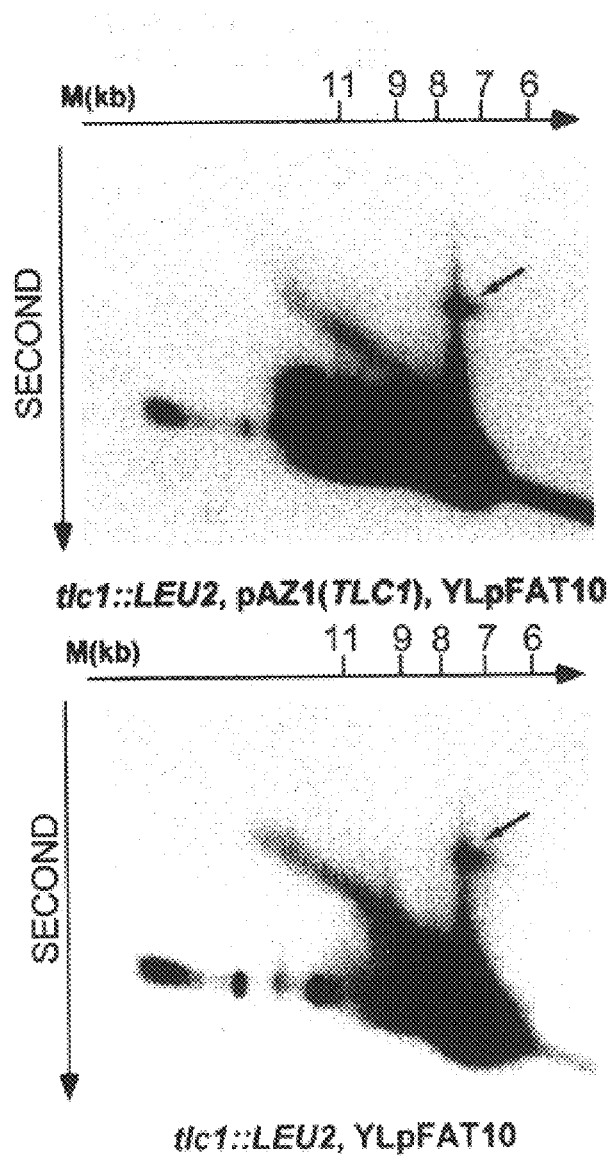

FIGS. 6A–6B. Telomere—telomere interactions in a strain lacking telomerase RNA. A yeast strain carrying a deletion of the TLC1 gene was transformed with the linear plasmid YLpFAT10 (FIG. 2A) and grown for ≧35 generations prior to DNA isolation and analysis. A) DNA of cells containing pAZ1 with TLCL (wt) or of cells devoid of pAZ1 (Δ) was digested with the indicated restriction enzymes and analyzed in an agarose gel using a telomere specific probe. Note that the terminal NsiI fragments of YLpFAT10 are about 2.5 and 3.5 kb respectively (FIG. 2A) and that there is no recognition site for XhoI in YLpFAT10. B) The replication intermediates of YLpFAT10 in exponentially growing cells were analyzed by two-dimensional agarose gel as described above. Left: cells also contained a plasmid born copy of the TLC1 gene (pAZI) and displayed no tlc1⁻-associated phenotypes; Right: tlc1⁻-cells which displayed tlc1⁻-associated phenotypes (telomere shortening, see above) and ultimately cell death (after 80–100 generations)(Dionne and Wellinger, in preparation). The probe for this gel was derived from pTRP1. The signal forming an arc above the diagonal of double-stranded DNA molecules corresponds to the conventional replication intermediates of YLpFAT10. The arrow points to the circular form of the plasmid which is held together by telomere—telomere interactions. The signal forming a smear at the position where high-molecular weight DNA migrated stems from genomic TRP1 sequences.

DETAILED DESCRIPTION

An in vitro system to study the behavior of telomere replication intermediates.

Figure 2A:
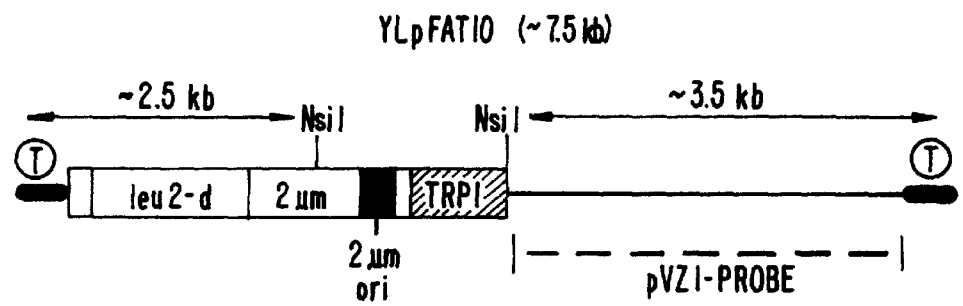
FIGS. 2A–2B. Plasmid constructs and schematic outline of the in vitro experiments. A) The structure of YLpFAT10. For construction of the plasmid, see Wellinger et al., 1993c. The relevant restriction sites and the sizes of the terminal fragments are indicated. B) The construction of plasmid pYLPV is described in detail in Wellinger et al., 1993c. It is a pBR322 based plasmid that contains the yeast ARSI sequences and two blocks of ~280 bp of yeast telomeric repeats (→) in an inverted orientation. In between these repeats are sequences from the yeast 2 $\mu$m DNA and LEU2 gene (Wellinger et al., 1993c). Plasmid pYLPVΔs is a derivative of pYLPV and its construction is described herein. Relevant restriction sites are indicated and the areas denoted as Probe A and Probe B are DNA fragments that were used as probes.
Figure 2B:
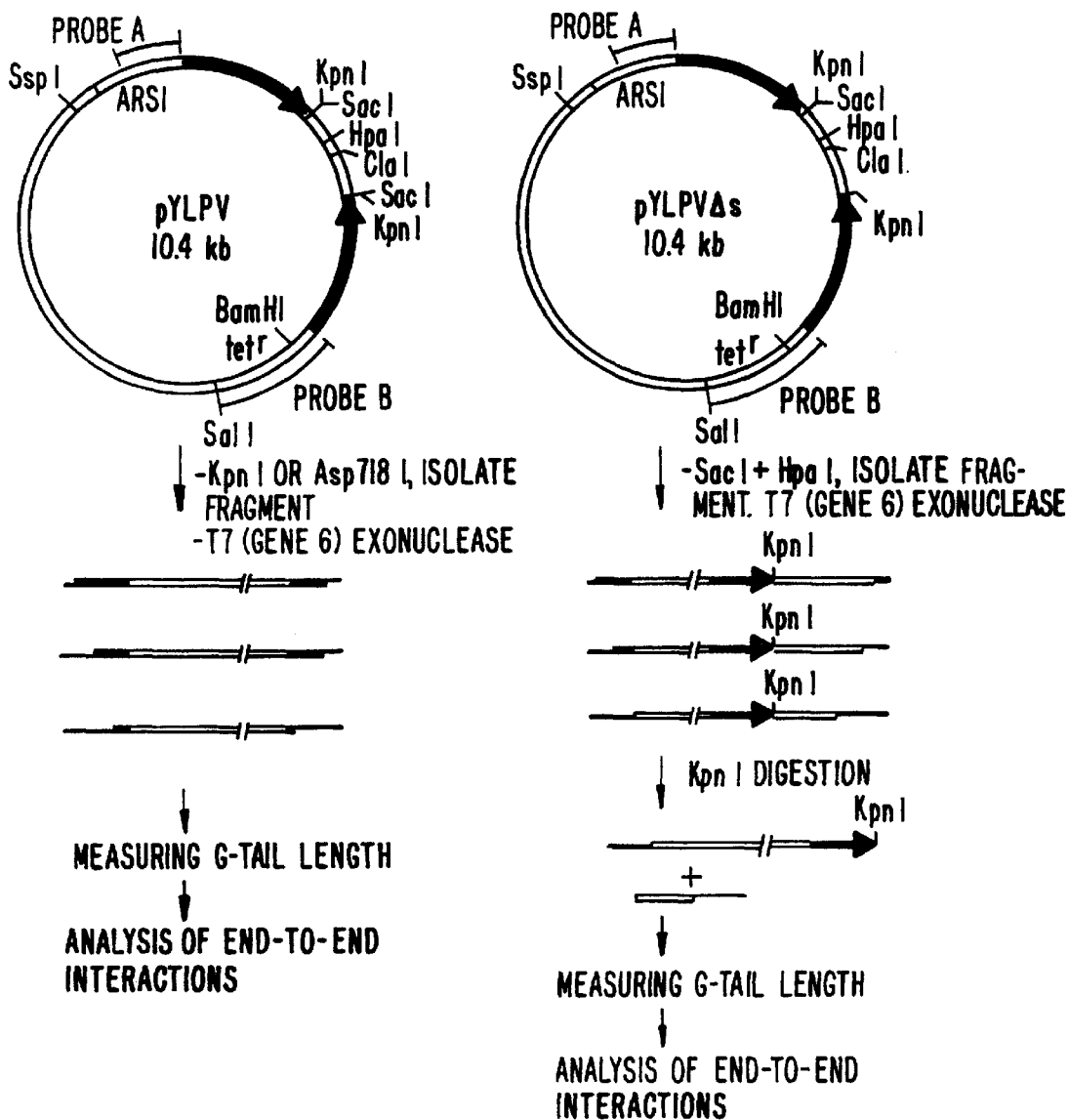

Using two dimensional agarose gel electrophoresis, the Applicant previously showed that the linear plasmid YLp-FAT10 (FIG. 2A) forms telomere—telomere associations that are dependent on the presence of in vivo generated $TG_{1-3}$ tails (Wellinger et al., 1993c). To explore the structural basis of the end-to-end interactions, the Applicant developed an in vitro system for producing molecules with terminal structures analogous to those expected for telomere replication intermediates generated in vivo. Briefly, two tracts of yeast telomeric repeats were cloned in an inverted orientation into a circular plasmid (see FIG. 2B and Wellinger et al., 1993c). Due to a common KpnI-restriction site at the end of both tracts, a ~7 kb linear fragment can be liberated that had a 4 base 3' overhang followed by ~280 bp of $C_{1-3}A/TG_{1-3}$ DNA at each end in the same orientation as the repeats exist in vivo. The Applicant then used a strand specific single stranded exonuclease to step-wise remove the 5' strands, effectively creating single stranded $TG_{1-3}$ tails of varying lengths on both ends (see FIG. 2B, left). Using a slightly modified plasmid, plasmids with $TG_{1-3}$ tails on one end and a block of double-stranded $C_{1-3}A/TG_{1-3}$ telomeric DNA on the other were also generated (FIG. 2B, right). These molecules mimic the two possible structures proposed for in vivo-generated replication intermediates of the short linear plasmid YLpFAT10, i.e. $TG_{1-3}$ tails on both ends of the plasmid or a $TG_{1-3}$ tail on one end and duplex telomeric DNA on the other.

Telomere—telomere interactions require a $TG_{1-3}$ tail on both interacting telomeres.

Figure 3A:
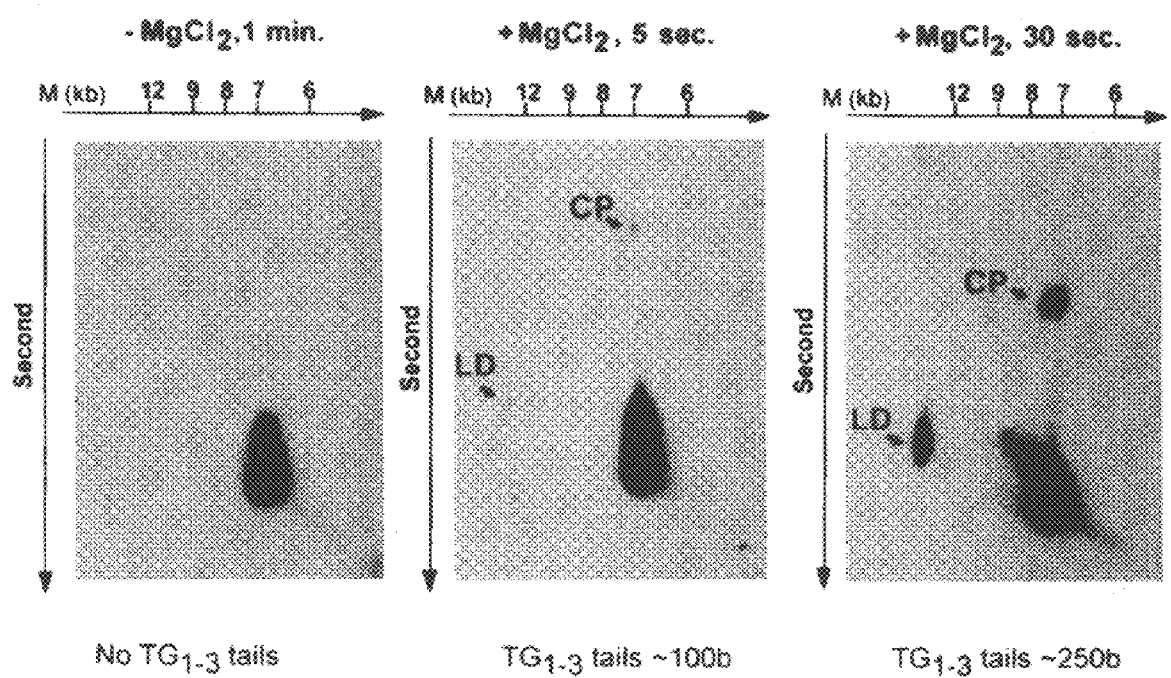
FIGS. 3A–3D. Analysis of molecules with $TG_{1-3}$ tails produced in vitro. A) Two-dimensional gel eletrophoresis of pYLPV molecules that had various lengths of $TG_{1-3}$ tails on both ends. For the first panel, the linearized DNA molecules were incubated with T7 (gene6) exonuclease in the absence of $MgCl_2$ for 1 min. The exonuclease is dependent on $MgCl_2$ and this DNA thus serves as negative control. For the second and third panel, the DNA was treated with the exonuclease for the indicated time prior to analysis by two-dimensional gel-electrophoresis (Brewer and Fangman, 1987; Brewer B. J. et al., 1988; Wellinger et al., 1993c). Tail length was measured as described (Wellinger et al., 1993c.). The directions of gel migration are indicated. CP: circular product; LD: linear dimer. B) Quantitative analysis of the relative amounts of LD and CP in two-dimensional agarose gels such as in A) versus the tail length of the molecules. Note that the relative amounts contributed by LD and CP were about equal for all tail lengths (see for example the gels in A). C) Electron microscopy of an aliquot of the DNA molecules analyzed in the third panel of A). LM: linear monomer; LD: linear dimer; CP: circular product. D) Top: Two-dimensional gel-electrophoresis of molecules with only one $TG_{1-3}$ tail. The molecules were derived from pYLPVΔs (see FIG. 2B) and had either no $TG_{1-3}$ tails (top left) or a $TG_{1-3}$ tail of ~150 bp on one end only (top right). As controls, molecules derived from pYLPVΔB (construction described herein) with either a $C_{1-3}A$ tail and a random tail (bottom left) or molecules with a $TG_{1-3}$ tail and a random tail (bottom right) were analyzed. Below each panel is a schematic outline of the molecules analyzed in the respective gel.
Figure 3B:
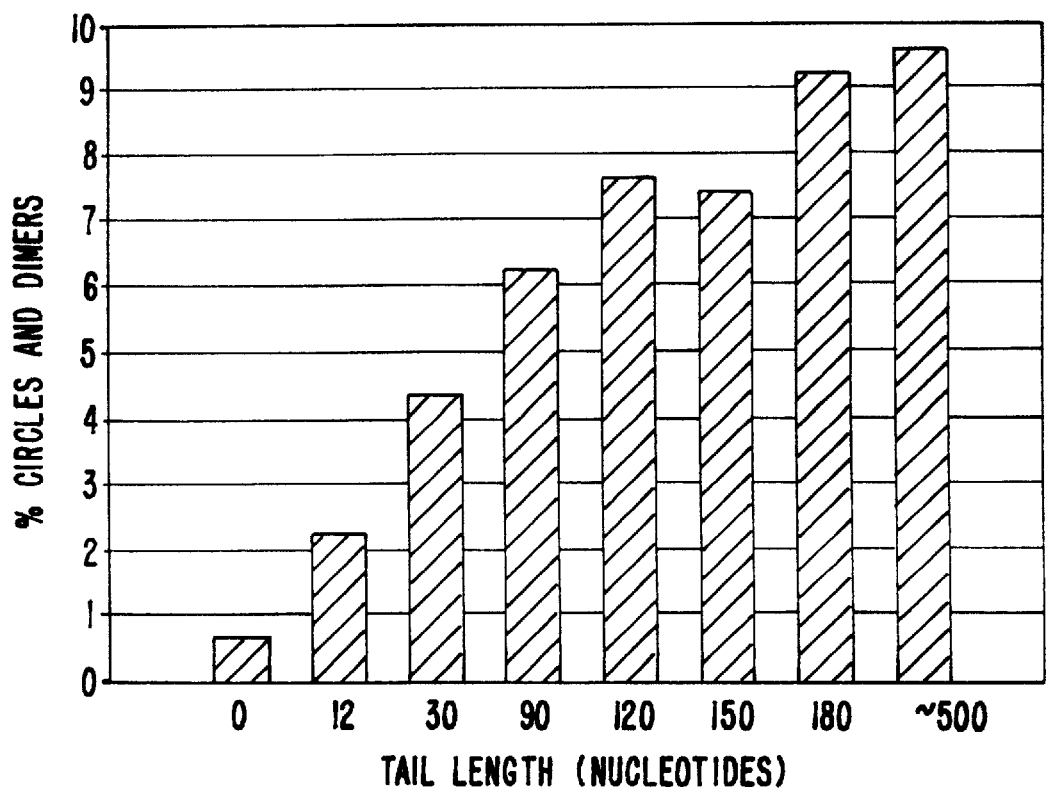

In vitro constructed molecules with $TG_{1-3}$ tails on both ends were subjected to the same two-dimensional gel analysis used to analyze the in vivo plasmid. In these gels, linear double-stranded DNA forms a diagonal whereas relaxed circular molecules migrate more slowly than linear molecules of the same mass in the second dimension and thus are separable from them (Brewer and Fangman, 1987). On the autoradiograph of such two-dimensional agarose gels, circular monomers (CP) as well as linear dimers (LD) of the original plasmids were readily detected (FIG. 3A). Independent of the length of the tails, we always observed about the same fraction of intramolecular interactions (circular molecules of unit length) as intermolecular interactions (linear dimers)(FIG. 3A). However, the total fraction of molecules with end-to-end interactions (i.e. the percentage of plasmids that were monomer circles or linear dimers) was dependent upon the length of the $TG_{1-3}$ tails: tails with fewer than 30 bases resulted in relatively few end-to-end interactions while longer $TG_{1-3}$ tails yielded up to 8–10% of molecules with end-to-end interactions (FIG. 3B).

Figure 3C:
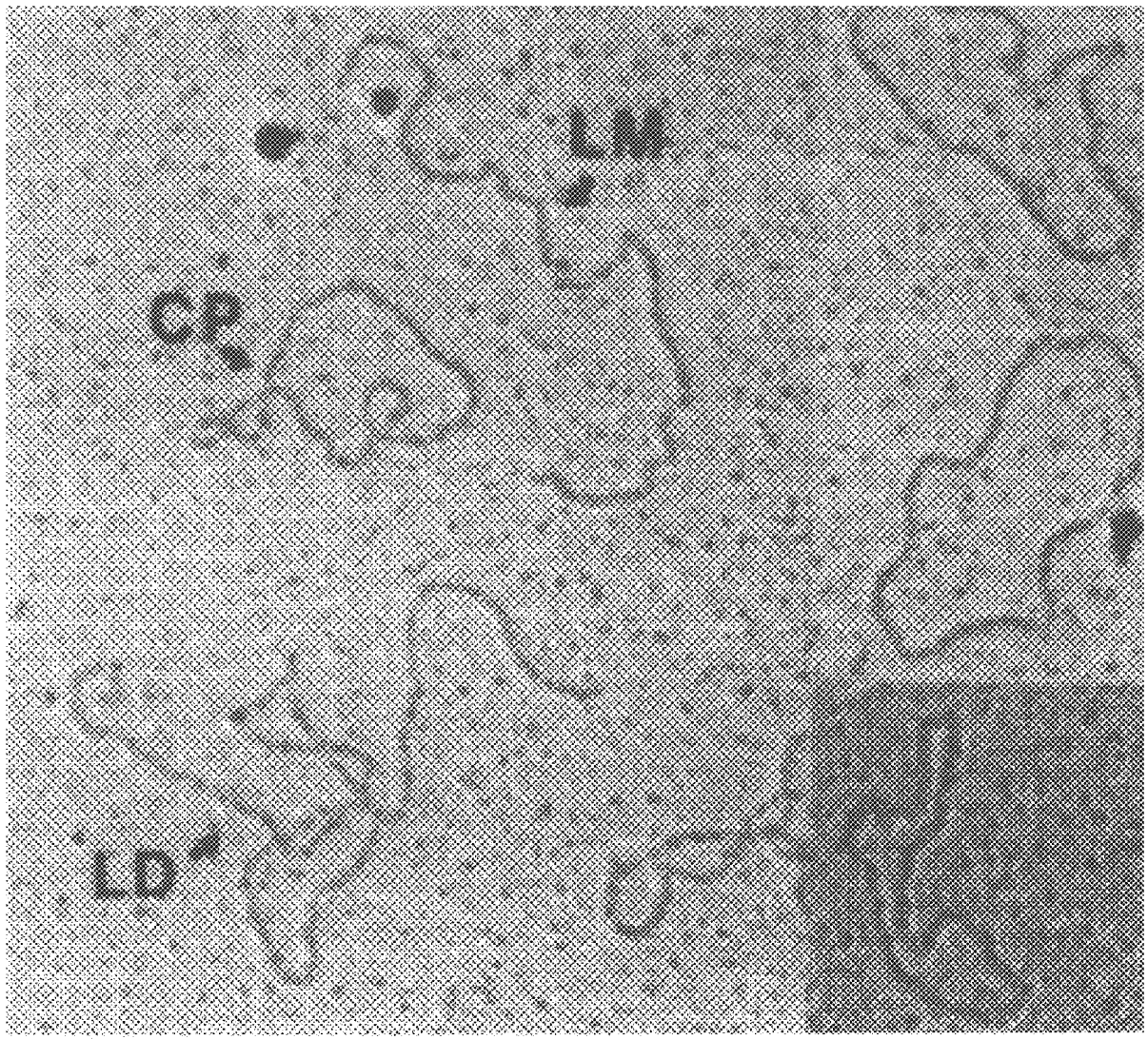

To verify the interpretation of the structured molecules detected by two-dimensional agarose gels, these preparations were also examined by electron microscopy. As with two-dimensional gels, monomer length linear molecules (LM), monomer circles (CP) and linear dimer (LD) molecules were observed (FIG. 3C). Thus, these experiments demonstrate that molecules with in vitro generated $TG_{1-3}$ tails at both ends can form end-to-end interactions as assayed by two-dimensional gel electrophoresis or electron microscopy. Moreover, since molecules on which all of the 5' strand of the telomeric repeats had been removed showed a maximal amount of end-to-end interactions, a double-stranded portion of the repeats was not required for these interactions (FIGS. 3A and 3B).

Figure 3D:
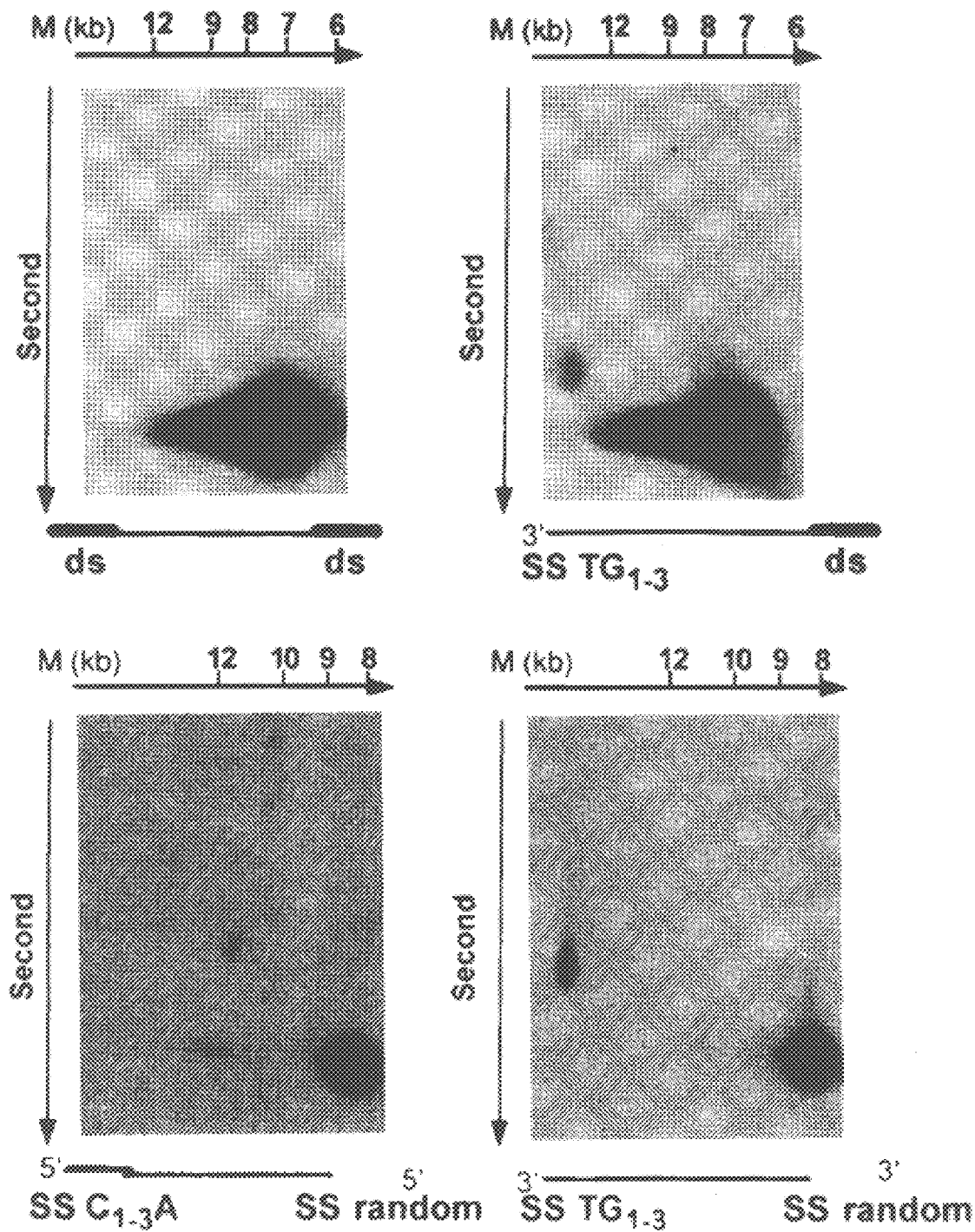

Next, molecules with a $TG_{1-3}$ tail on one end and a double-stranded block of telomeric repeats on the other were analyzed in the same fashion. The linear fragment used in this experiment was isolated from plasmid pYLPVΔs as outlined in FIG. 2B. A $TG_{1-3}$ tail of ~150 bases was exposed on one end while the other end contained a 280 bp block of double-stranded $C_{1-3}A/TG_{1-3}$ telomeric repeats, about the length of an in vivo telomere (see FIG. 2B). These molecules as well as molecules without $TG_{1-3}$ tails were then analyzed on two-dimensional gels as above (FIG. 3D, top panels). As expected, molecules without tails showed no end-to-end interactions (see also FIG. 3A). When molecules with a $TG_{1-3}$ tail at one end and duplex telomeric DNA at the other end were analyzed, a signal corresponding to linear dimers was observed (FIG. 3D, top right). On some gels, a weak signal for monomer circular DNA was also observed (data not shown), but such end-to-end interactions between a $TG_{1-3}$ tail and a double-stranded block of telomeric repeats were never detectable using a one-dimensional gel assay (see below). In molecules with a $TG_{1-3}$ tail at one end only, linear dimers could arise either by interactions between ends where both ends had $TG_{1-3}$ tails or where one end had a $TG_{1-3}$ tail and the other end was duplex. however, monomer circles could only form between an end with a $TG_{1-3}$ tail and a duplex end. Thus, the absence of monomer circles suggest that an end with a $TG_{1-3}$ tail could not interact with a duplex end and that the linear dimers observed were formed by interactions of two ends with $TG_{1-3}$ tails (see also below).

As controls, molecules with a $C_{1-3}A$ tail at one end of the plasmid and a random sequence tail at the other as well as molecules with a $TG_{1-3}$ tail at one end and a random tail at the other were produced from plasmid pYLPVΔB. While the molecules with a $C_{1-3}A$ tail did not yield any end-to-end interactions (FIG. 3D, bottom left), the molecules with one end having a $TG_{1-3}$ tail and the other having a random sequence again produced linear dimer molecules (FIG. 3D, bottom right), indicative of end-to-end interactions mediated by the $TG_{1-3}$ tails. These results suggest that only $TG_{1-3}$ tails support end-to-end interactions and that a $TG_{1-3}$ tail is required on both ends that interact.

Figure 4A:
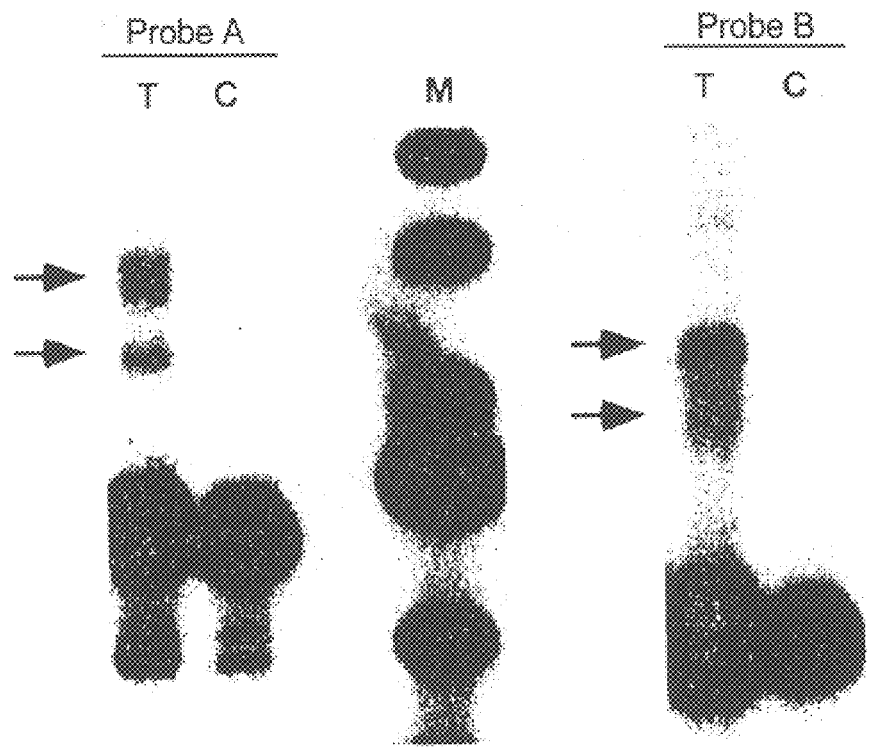
FIGS. 4A–4B. Analysis of junction fragments generated in vitro. A) The linear fragment derived from plasmid pYLPV was reacted with T7 (gene6) exonuclease to produce $TG_{1-3}$ tails of ~200 bases at each end (FIG. 2B). The resulting molecules were then digested with the restriction enzymes SspI and SalI and the fragments analyzed by Southern blotting. On the left is an autoradiogram of the gel after hybridization with probe A (see FIG. 2B). T: molecules with $TG_{1-3}$ tails; C: control, molecules did not have tails; M.

To establish firmly that telomere—telomere interactions only occur if the interacting telomeres both had a $TG_{1-3}$ tail, the junction fragments generated by telomere—telomere interactions were analyzed. The linear fragment from pYLPV was isolated and $TG_{1-3}$ tails of ~200 bases were exposed as described above on both ends of the linear DNA. This DNA was then digested with the restriction enzymes SspI and SalI prior to one-dimensional gel electrophoresis and Southern analysis. The terminal fragment recognized by probe A is ~1.3 kb and the terminal fragment recognized by probe B is ~0.95 kb (FIG. 2B and FIG. 4A, heaviest signal). If these terminal fragments, which all terminate in $TG_{1-3}$ tails, interact with each other, three junction fragments are expected: probe A should detect A-A associations, which generate a ~2.6 kb fragment, and A-B associations, which generate a ~2.25 kb fragment. Fragments corresponding to these sizes were indeed detected on the autoradiogram (FIG. 4A left, indicated by arrows). When the same blot was rehybridized with probe B, the ~2.25 kb fragment (A-B fragment) and a fragment resulting from the association of two B-ends (~1.9 kb) were detected (FIG. 4A right, indicated by arrows). Thus, this one-dimensional gel analysis of restriction enzyme digested DNA detected all the end-to-end junction fragments predicted from the two-dimensional gel analysis: those arising from an intramolecular interaction (circularization of the plasmid yielding an A-B interaction) and those arising from intermolecular interactions (formation of linear dimer molecules that can be held together by A-A, A-B or B-B interactions).

Figure 4B:
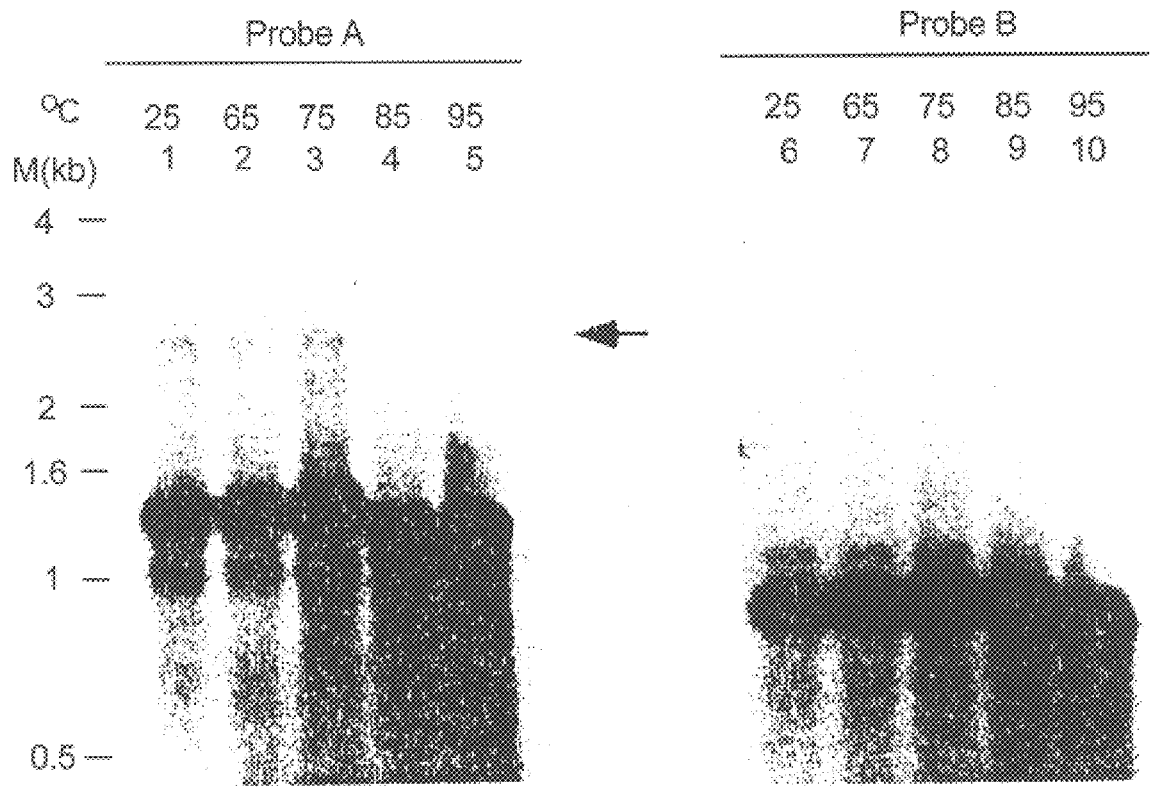

In addition, linear DNA fragments with a ~200 base $TG_{1-3}$ tail on the A-end and ~280 bps of duplex $C_{1-3}A/TG_{1-3}$ DNA at the B-end were generated in vitro, digested with SspI and SalI to release the junction fragment, and analyzed as above. After hybridization of the blot to probe A, restriction fragments corresponding to the A-ends (~1.3 kb) and to the A-A junction (~2.6 kb) were observed (FIG. 4B, lane 1). However, no A-B junctions (~2.25 kb) were observed with either the A or B probes (FIG. 4B, lanes 1 and 6). Thus, as already suggested by the two-dimensional gel assay, in order to form a stable junction fragment, both participating ends required $TG_{1-3}$ tails.

End-to-end interactions of in vivo synthesized molecules have a thermal stability similar to that of in vitro generated molecules.

In order to examine the nature of the end-to-end interactions, the Applicant investigated the thermal stability of the junction fragment formed by telomere—telomere interactions of in vivo and in vitro generated molecules. When DNA containing YLpFAT10 and isolated from cells in late S-phase was digested with NsiI, a fragment of about 6 kb is detected on a Southern blot (FIG. 5A, lane 6 indicated by an arrow, and Wellinger et al., 1993c). This fragment hybridizes to probes specific for both ends of the plasmid (Wellinger et al., 1993c) and was not observed in DNA from G1 arrested cells (FIG. 5A, lane 1). In addition to this fragment, the probe detected bands of ~5 kb and ~7.5 kb which correspond in size and hybridization properties to partial digestion products of linear YLpFAT10 molecules (FIGS. 2A and 5A). The probe also detected a 3.5 kb band (heavy signal in FIG. 5A) generated from the right telomere of the linear YLpFAT10 molecule (FIG. 2A). If the 6 kb fragment reflects the junction fragment formed by the intramolecular telomere—telomere interactions and thus reflects the circular form of YLpFAT10 observed in the two-dimensional gel assays (Wellinger et al., 1993c), the circular form and the junction fragment should be present in the same relative amounts in the same DNA sample. When the relative amount of circular forms observed in the two-dimensional gels was quantitated and compared to the relative amount of the junction fragment observed in the one-dimensional gel, no significant difference was found (table 1). This suggests that the two-dimensional and one-dimensional gel assays are detecting the same population of molecules. Taken together, these experiments demonstrate that the 6 kb NsiI fragment corresponds to a junction fragment formed by an interaction of two telomeres of YLpFAT10.

To determine the stability of the telomere—telomere interactions on in vivo generated molecules, NsiI digested DNA was exposed to short incubations at various temperatures and immediately loaded onto an agarose gel and analyzed by Southern hybridization (FIG. 5A, lanes 7–10). The junction fragment was stable up to 72° C. but was completely absent after incubation at 78° C. (compare lanes 9 and 10, FIG. 5A). This disappearance was not due to a general denaturation of the DNA since both the weak partial digests as well as the main terminal restriction fragment remained largely intact at this temperature (FIG. 5A, lane 10). This experiment demonstrates that the two telomeres in the junction fragment were held together by non-covalent interactions that dissociate between 72° C. and 78° C.

To determine the thermal stability of the junction fragment on in vitro generated molecules, linear DNA fragments with a ~200 base $TG_{1-3}$ tail on the A-end and ~280 bps of duplex $C_{1-3}A/TG_{1-3}$ DNA at the B-end were generated, treated with SspI and SalI to release the A-A junction fragments, incubated briefly at elevated temperatures, and then subjected to agarose gel electrophoresis and Southern hybridization. As seen for the YLpFAT10 DNA isolated from yeast cells, the junction fragment was stable up to about 75° C. and was not observed after incubations at higher temperatures (FIG. 4B, lanes 2–5). Therefore, the junction fragments of in vivo and in vitro generated molecules had a similar thermal stability, consistent with the possibility that they are maintained by the same type of interactions, that is, the association of two $TG_{1-3}$ tails.

Further support for this interpretation comes from the behavior of undigested in vivo generated YLpFAT10 molecules after heat treatment. After heating the DNA to 78° C., which completely eliminated telomere—telomere interactions as monitored by loss of the junction fragment (FIG. 5A), the DNA was cooled to room temperature and loaded on a two-dimensional agarose gel. About the same amount of the circular form of the plasmid (CFP, see also Wellinger et al., 1993c) relative to total DNA was detected before and after heating (FIG. 5B). In this experiment, the reforming of CFP after heating occurred in vitro with purified DNA and in the absence of any cellular proteins. Therefore, these interactions, like those detected on in vitro generated molecules, must occur on molecules with a $TG_{1-3}$ tail on both ends. Taken together, these data argue that the YLpFAT10 molecules generated in vivo and that form CFP had a $TG_{1-3}$ tail at each end.

$TG_{1-3}$ tails are generated in vivo in the absence of telomerase RNA.

Figure 1A:
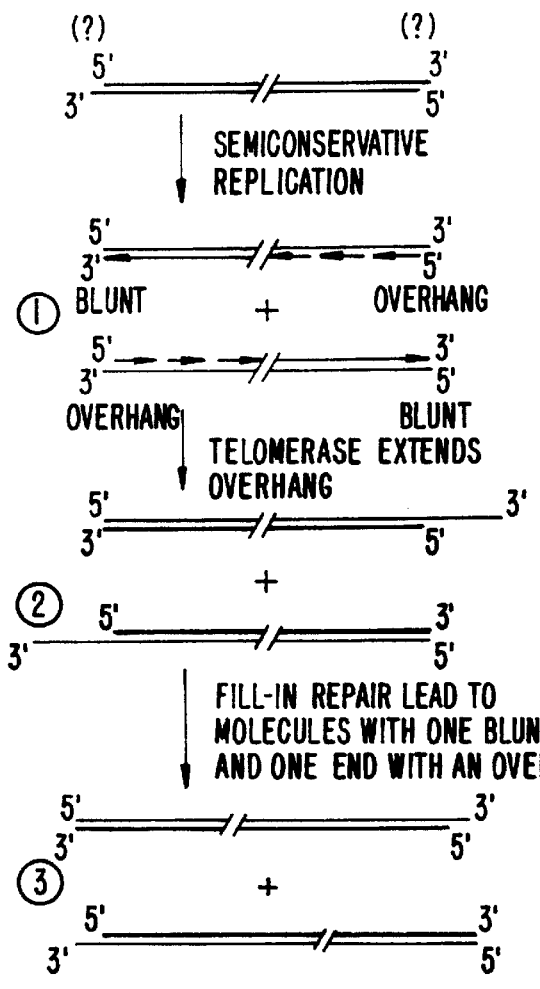
FIGS. 1A–1B. Models for telomere replication and maintenance in yeast. The actual structure of the telomeric DNA at the very ends of the chromosomes is unknown ("?" on top). However, it has been proposed that a short 3'-overhang is a conserved feature of eukaryotic chromosome ends (see for example, Lingner et al., 1995; Zakian, 1995). A) The conventional replication mechanisms (1) and telomerase mediated strand elongation (2) will ultimately yield molecules with one end having a blunt end and the other end having a short 3'-overhang (3). B) The model for telomere maintenance incorporating the results of the present study. After replication, a strand-specific exonuclease exposes $TG_{1-3}$ tails on both telomeres of individual molecules (2) which are processed to generate short 3'-overhangs on all telomeres (3).

Given the biochemical properties of telomerase, current models of telomere replication predict the occurrence of $TG_{1-3}$ tails on only one end of individual daughter molecules (FIG. 1A). Thus, if, as the Applicant's data suggest, linear plasmids have a $TG_{1-3}$ tail at both telomeres, the tails present on the ends replicated by leading strand synthesis must be generated by a mechanism other than telomerase. To test this possibility directly, we analyzed YLpFAT10 replication intermediates in a strain lacking TLC1, the gene encoding telomerase RNA (Singer and Gottschling, 1994). The chromosomal copy of TLC1 was deleted in a strain carrying the plasmid pAZ1 which bears the wild type TLC1 gene; this tlc1 Δ strain carrying pAZ1 served as the control for the experiment. Cells that lost pAZ1 were identified and allowed to grow for at least 35 generations before DNA was isolated from exponentially growing cells and examined for $TG_{1-3}$ tails and CFP. Although cells can grow for 50–100 generations without TLC1 (Singer and Gottschling, 1994), telomeres on both plasmid and chromosomal telomere were shorter than in control cells after 35 generations without TLC1 (FIG. 6A), demonstrating phenotypically that these cells lack telomerase.

The same DNA samples used to determine telomere lengths were analyzed by two-dimensional agarose gels as described above. Circular forms of YLpFAT10 (CFP) were equally abundant in the tlc1 Δ and control strains (FIG. 6B). In independent experiments, a non-denaturing in gel hybridization technique was used to show that the telomeres in a tlc1 Δ strain acquire $TG_{1-3}$ tails late in S-phase and the presence of the tails correlates with plasmid circularization (Dionne and Wellinger, to be published elsewhere). Thus, $TG_{1-3}$ tails and the interactions they support are generated in late S-phase in a strain lacking telomerase. Consistent with this result, $TG_{1-3}$ tails and plasmid circularization were also detected in an est1 Δ strain (Wellinger, Wolf, and Zakian, data not shown), where EST1 encodes a putative protein component of telomerase (Lin and Zakian, 1995). Since plasmid circularization requires a $TG_{1-3}$ tail on both ends (FIGS. 3, 4), these data suggest that regardless of whether an end is replicated by leading or lagging strand synthesis, it acquires a $TG_{1-3}$ tail by a telomerase-independent, cell cycle regulated mechanism.

Discussion.

Due to the polarity of conventional DNA polymerases, half of the telomeres are replicated by lagging strand synthesis and the other half by leading strand synthesis (FIG. 1, Lingner et al., 1995; Zakian, 1995). Lagging strand synthesis always copies the G-rich strand and leading strand synthesis always copies the C-rich strand. Thus, the current model predicts that half of the telomeres will have a gap on the 5' end of the newly synthesized C-strand, exposing a short G-rich tail. The other half of the telomeres is expected to be blunt ended (FIG. 1A). In vitro, telomerase requires a short single stranded substrate of the G-rich strand (3'-end) for telomere repeat addition suggesting that in the absence of additional factors, it will only generate a $TG_{1-3}$ tail on one end of a linear DNA molecule (Greider and Blackburn, 1985; Lingner et al., 1995, and for review Blackburn, 1992).

In the present study, the Applicant constructed in vitro molecules with a $TG_{1-3}$ tail on one end and a duplex block of $C_{1-3}A/TG_{1-3}$ sequences on the other end or with $TG_{1-3}$ tails on both ends (FIGS. 3, 4). Stable interactions were not detected between an end with a $TG_{1-3}$ tail and an end with duplex telomeric DNA (FIGS. 3, 4). Independent experiments to detect associations of G-rich telomeric oligomers with duplex telomeric DNA via G·G:C triplex formation also failed (data not shown). In contrast, molecules with two $TG_{1-3}$ tails readily formed end-to-end interaction (FIGS. 3, 4). The formation of these telomere—telomere interactions was rapid, did not require high concentrations of cations, the presence of $Mg^{++}$ or even a short stretch of duplex telomeric repeats on the interacting telomeres (FIGS. 3, 4). In addition, preliminary results suggest that telomere—telomere interactions are not prevented by DMS methylation at the N7 of the guanines. Taken together, these data argue that the telomere—telomere interactions did not occur by either a triple helix or a G-quartet mediated association. Although the exact base pairing scheme responsible for the interactions has not been determined, our results are most consistent with a model in which the $TG_{1-3}$ tails interact to form duplex DNA held together by G:G bps. A maximum of ~10% of the telomeres formed telomere—telomere interactions (FIG. 3B), even after incubations for up to three days at 37° C. and even though the $TG_{1-3}$ tails were generated in a way that ensured that about the same number of bases were removed from all molecules (Wellinger et al., 1993a, c, and data not shown). Although the $TG_{1-3}$ tails of the majority of the molecules did not interact with other telomeres with $TG_{1-3}$ tails, it is possible that these $TG_{1-3}$ tails formed intra-strand fold back structures involving G:G base pairing.

The most straightforward interpretation of all the data is that the same telomere—telomere interactions are formed on in vivo and in vitro generated molecules. This interpretation argues that in vivo generated molecules contain $TG_{1-3}$ tails on both ends of individual molecules. The current model of telomere replication predicts that telomerase can generate a $TG_{1-3}$ tail on only one end of a molecule (FIG. 1A). Moreover, $TG_{1-3}$ tails were present on telomeres in cells that lacked Est1p (Wellinger, Wolf and Zakian, unpublished), a putative component of yeast telomerase (Lin and Zakian, 1995), and in cells lacking the TLC1 gene (FIG. 6) which encodes telomerase RNA (Singer and Gottschling, 1994).

Figure 1B:
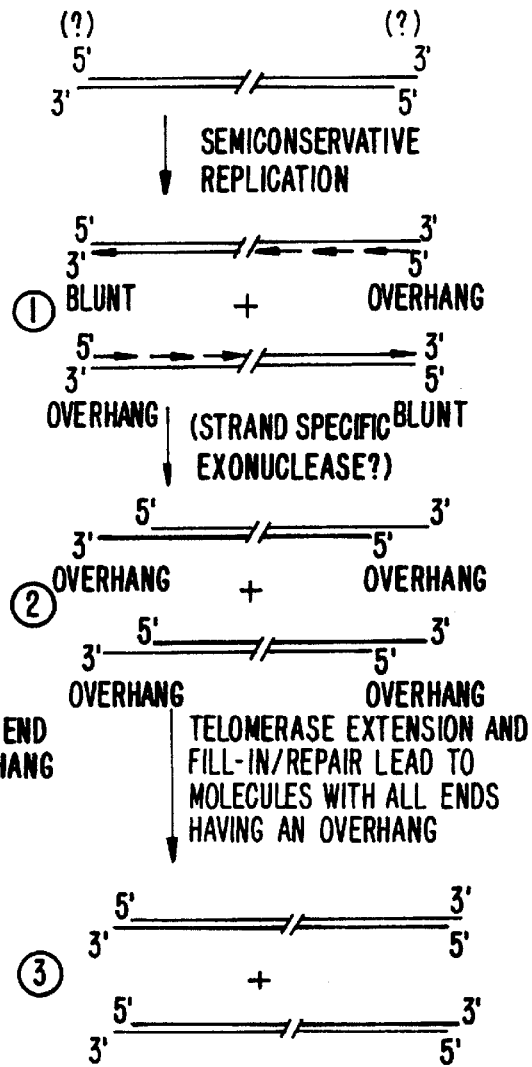

Therefore, we favor a model in which a strand specific 5'→3' exonuclease generates a $TG_{1-3}$ tail at each telomere (FIG. 1B). The Applicant proposes that the cell cycle controlled degradation of the $C_{1-3}A$ strand is regulated by the essential protein Cdc13p, since cells lacking this protein contain long stretches of single stranded DNA of the predicted polarity in telomeric and sub-telomeric regions of the chromosome (Garvik et al., 1995). In this model, Cdc13p would limit the extent of exonuclease digestion or regulate fill-in repair synthesis after the $TG_{1-3}$ tails are exposed. Exonuclease generated $TG_{1-3}$ tails create a structure that allowed all telomeres to be a substrate both for telomerase and for terminus binding proteins (FIG. 1B). Although telomerase-mediated strand elongation is not essential in every cell cycle (Lundblad and Szostak, 1989; Singer and Gottschling, 1994; McEachern and Blackburn, 1995), generating a substrate for teminus binding proteins is likely to be an obligatory step in telomere maintenance.

The involvement of exonucleases in recombination and repair is well documented in prokaryotes and eukaryotes (for review, see Sadowski, 1985). In yeast, spontaneous and HO-induced double-stranded breaks are processed to molecules with a long single stranded 3' overhang (Cao et al., 1990; White and Haber, 1990; Sun et al., 1991). Moreover, a 5'→3' exonuclease required for in vitro recombination was identified from yeast extracts (Huang and Symington, 1993). These exonucleolytic activities normally associated with recombination or repair might also act on telomeres. Alternatively, a 5'→3' exonuclease associated directly with the replication fork or with telomerase may produce these overhangs. It has been proposed that FEN-1, a structure specific DNA endonuclease that also contains a 5'→3' exonuclease activity, is associated with the DNA replication machinery. RAD27, a yeast homologue of FEN-1, has similar biochemical activities (Harrington and Lieber, 1994). The $TG_{1-3}$ tails may thus serve for both initiation of recombination as well as substrates for telomerase. Consistent with this hypothesis, long term survivors of an Est1p-deficiency are able to maintain their telomeres via gene conversion type recombination events (Lundblad and Blackburn, 1993). Furthermore, heterologous telomeric repeats at the two opposite ends of a linear plasmid can recombine via a gene conversion type of recombination event or be used by telomerase for telomeric repeat addition (Pluta and Zakian, 1989; Wang and Zakian, 1990).

In summary, the results reported here suggest that single stranded $TG_{1-3}$ tails are generated at the end of S-phase on telomeres, irrespective of whether the telomeres were replicated by leading or lagging strand synthesis. These data thus suggest that unexpected enzymatic activities other than telomerase generate these $TG_{1-3}$ tails and that their generation is an integral step in telomere maintenance.

EXAMPLES

Yeast and *E. coli* Strains.

Yeast cells were transformed as described (Schiestl and Gietz, 1989) and propagated in standard media (Zakian and Scott, 1982). The yeast strain used to isolate replication intermediates was RM14-3A (Mata, his6, bar1, trp1-289, leu2-3, 112, ura3-52, cdc7-1) (McCarroll and Fangman, 1988). Cell synchronization using both of two consecutive blocks (α-factor and cdc7) has been described previously (Brewer and Fangman, 1987; Wellinger et al., 1993b, c). The DNAs used in this study were derived from cells arrested in G1 by α-factor, from cells that had been released for 27 min into S-phase (FIG. 5A) and from cells that had been released for 28 min into S-phase (FIG. 5B). This is the time period in the synchronized S-phase during which there are maximal amounts of $TG_{1-3}$ tails on yeast telomeres (Wellinger et al., 1993c). The tlc1Δ strain was obtained as follows: strain UCC3535 (Mata/MAtα, ura3-52/ura3-52, lys2-801/lys2-801, ade2-101/ade2-101, his3-Δ200/his3Δ200, trp1-Δ1/trp1-Δ1, leu2-Δ1/leu2-Δ1, DIA5-1/DIA5-1, TLC1/tlc1::LEU2) (obtained from M. Singer and D. Gottschling, unpublished) was first transformed with plasmid pAZ1 (Beeler et al., 1994) which is a pRS316 (Sikorski and Hieter, 1989) derivative containing genomic copies of the URA3 and TLC1 genes. Cells were then sporulated and random Leu⁺/Ura⁺ spores were isolated. The linear plasmid YLp-FAT10 (see below) was introduced into these haploids as described (Wellinger et al., 1993c) using the TRP1 gene on YLpFAT10 as selective marker gene. This strain thus carried a deletion of the TLC1 gene that was complemented by pAZ1 and also contained the linear plasmid YLpFAT10. Such cells were plated on FOA-trp plates to select for cells that had lost pAZ1 and were subsequently grown in YC-trp media for at least 35 generations prior to DNA isolation and analysis. At least theoretically, such an outgrowth is sufficient to dilute out molecules that were present at $7 \times 10^{10}$ copies per cell in the starting culture. DNA was isolated from yeast nuclei obtained by minor modifications (Wellinger et al., 1993c) of a glass bead procedure (Huberman et al., 1987). All plasmid constructions were cloned in *E. coli* strain MC1066 (r⁻m⁺, trpC9830, leuB6, pyrF74::Tn5, lacΔx74, strA, galU, galK) (Casadaban et al., 1983).

Plasmid constructions.

The construction of the circular plasmid YEpFAT10 and its linear derivative YLpFAT10 have been described (Wellinger et al., 1993c, see FIG. 2A). Plasmid pYLPV is as described in (Wellinger et al., 1993c, see FIG. 2B). pYLPVΔs was obtained by partially digesting pYLPV with SacI and removing the 3' overhangs with T4 DNA polymerase in the absence of nucleotides.

The resulting plasmids were recircularized by ligation and transformed into *E. coli*. pYLVΔB is a derivative of pYLPVΔs. pYLPVΔs was digested with ClaI and BamHI and the fragment containing one block of telomeric repeat was replaced by a 365 bp ClaI/BamHI fragment of pBR322 (Sutcliffe, 1978). The resulting plasmid pYLPVΔB is 8.2 kb and has one block of telomeric repeats derived from pYLPV. At the distal end of these repeats are unique KpnI and SacI sites, with which the plasmids were linearized for the experiments in FIG. 3. After the treatment with the T7 (gene6) exonuclease or the T4 DNA polymerase, single strands of the indicated polarity are exposed. Note that in all cases, the ends of the linear DNA molecules after KpnI digestion have the following sequence: 5'- . . . GTGTGGTGTGGGTAC-3' (SEQ ID NO: 1) (underlined are nucleotides stemming from the KpnI site). Thus only the very last two nucleotides do not conform to telomeric repeat DNA on this strand. The sequences denoted 'random' are derived from the tetracyclin resistance gene of pBR322. pvtet is the plasmid pVZ1 (Henikoff and Eghtedarzadeh, 1987) into which a 0.62 kb HindIII-SalI fragment comprising the tetracycline resistance gene from pBR322 was cloned. PAHB and pTRP1 were obtained, respectively, by cloning a 235 bp BglII-HindIII fragment and a 827 bp EcoRI-StuI fragment derived from the TRP1ARS1 sequences of YRp7 (Stinchcomb et al., 1980) into the BamHI-HindIII and EcoRI-SmaI sites of pVZ1.

Formation of 3' overhangs in vitro.

The technique used to obtain $TG_{1-3}$ tails of defined sizes was described in detail previously (Wellinger et al., 1993a, c). Briefly, all the $TG_{1-3}$ tails were obtained by linearizing the respective plasmids with the indicated enzymes and subsequent treatment of the ends with T7 (gene6) exonuclease (US Biochemicals). Using these conditions, the strand forming the 5' end of all the double-stranded molecules can be removed in a controlled way (Kerr and Sadowski, 1972; Wellinger et al., 1993c). An aliquot of all reactions was then treated briefly with mung bean nuclease (Boehringer) to remove the $TG_{1-3}$ tails and the resulting fragments were sized on an agarose gel (Wellinger et al., 1993a, c). The difference in length of these molecules as compared to the input molecules provides a measure of the length of the $TG_{1-3}$ tails left after the T7 (gene6) exonuclease treatment (Wellinger et al., 1993a, c, and data not shown). To produce the tails of the opposite strand as described for the control molecules in FIG. 3, the isolated DNA fragments were treated with T4 DNA polymerase in the absence of dNTPs and the lengths of the resulting tails were determined as above.

DNA analysis.

One- and two-dimensional agarose gel techniques, Southern blotting and hybridization conditions were described previously (Brewer and Fangman, 1987; Runge and Zakian, 1989; Wellinger et al., 1993c). DNA size standards on all gels were end labeled "ladder" DNA (Gibco-BRL). Riboprobes were created by in vitro transcription by T3 RNA polymerase of linearized plasmids in the presence of $\alpha$-$^{32}$P-labeled CTP (Wahl et al., 1987). DNAs used were pVZ1 (Henikoff and Eghtedarzadeh, 1987), pAHB (probe A). pvtet (probe B) (see FIG. 2 for location of probes A and B) and pTRP1. For the gel in FIG. 6A, an in-gel hybridization technique using a $^{32}$P-end-labeled oligonucleotide was used (Counter et al., 1992). In cases where the radioactive signals were quantified, a Molecular Dynamics 400A PhosphorImager with the ImageQuant software was used (Johnston et al., 1990).

The thermal stability of the end-to-end interactions for the in vitro constructed molecules were analyzed by first isolating the respective linear fragments from an agarose gel (see FIG. 2B). These fragments were then treated with T7 (gene6) exonuclease as described above. The resulting DNA was subsequently digested with SspI and SalI. 15 mM EDTA and 0.5% SDS were added and the DNA was extracted once with phenol/chloroform and ethanol precipitated in the presence of 150 mM NaCl and 10 μg glycogen (Boehringer). DNA pellets were washed in 70% ethanol and resuspended in $H_2O$. These samples were then incubated for 10 min at the indicated temperatures, removed to ice and immediately loaded onto a 1% agarose gel. The expected terminal restriction fragments after this digestion are 1.3 kb for the SspI end (A end) and 0.95 kb for the SalI end (B end)(see FIG. 1B). For the in vivo synthesized YLpFAT10 molecules, the DNA was digested with NsiI (Wellinger et al., 1993c), and then treated exactly as described above for the in vitro molecules. The terminal restriction fragments were expected to be ~3.5 and ~2.5 kb in size (see FIG. 2A). Since these fragments were functional telomeres in vivo, their size is somewhat heterogenous. The junction fragment resulting from end-to-end interactions is expected to be ~6 kb (Wellinger et al., 1993c).

Electron microscopy.

For electron microscopy, molecules were spread by the cytochrome c method (Sommerville and Scheer, 1987). Samples were picked up on parlodion coated grids, stained with uranyl-acetate and rotary shadowed. Specimens were examined in a JEOL 100Sx microscope and photographed. Contour measurements were done on a Houston Instruments Hipad™ digitizer attached to a DEC Rainbow computer. The data was analyzed using a GW-basic program (A. Taylor, unpublished). At least 20 molecules of each species were measured and compared to standard molecules.

REFERENCES

Beal, P. A., and Dervan, P. B. (1991). Second structural motif for recognition of DNA by oligonucleotide-directed triple-helix formation. Science 251, 1360–1363.

Beeler, T., Gable, K., Zhao, C., and Dunn, T. (1994). A novel protein, CSG2p, is required for $Ca^{2+}$ regulation in Saccharomyces cerevisiae. J. Biol. Chem. 269, 7279–7284.

Blackburn, E. H. (1992). Telomerases. Annu. Rev. Biochem. 61, 113–129.

Brewer, B. J., and Fangman, W. L. (1987). The localization of replication origins on ARS plasmids in Saccharomyces cerevisiae. Cell 51, 463–71.

Brewer, B. J., Sena, E. P., and Fangman, W. L. (1988). Analysis of replication intermediates by two-dimensional agarose gel electrophoresis. Canc. Cells 6, 229–234.

Cao, L., Alani, E., Kleckner, N. (1990). A pathway for generation and processing of double-strand breaks during meiotic recombination in S. cerevisiae. Cell 61, 1089–1101.

Cardenas, M. E., Bianchi, A., and de Lange, T. (1993). A Xenopus egg factor with DNA-binding properties characteristic of terminus-specific telomeric proteins. Genes & Development 7, 870–882.

Casadaban, M. J., Martinez-Arias, A., Shapira, S. K., and Chou, J. (1983). Beta-Galactosidase gene fusions for analyzing gene expression in Escherichia coli and yeast. Methods Enzymol. 100, 293–308.

Cheng, A. J., and Van Dyke, M. W. (1993). Monovalent cation effects on intermolecular purine-purine-pyrimidine triple-helix formation. Nucleic Acids Res. 21, 5630–5635.

Counter, C. M., Avilion, A. A., LeFeuvre, C. E., Stewart, N. G. Greider, C. W., Harley, C. B., and Bacchetti, S. (1992). Telomere shortening associated with chromosome instability is arrested in immortal cells which express telomerase activity. Embo J. 11, 1921–1929.

Garvik, B., Carson, M., and Hartwell, L. (1995). Single-stranded DNA arising at telomeres in cdc13 mutants may constitute a specific signal for the RAD9 checkpoint. Mol. Cell. Biol. 15, 6128–6138.

Gellert, M., Lipsett, M. N., and Davies, D. R. (1962). Helix formation of guanylic acid. Proc. Natl. Acad. Sci. U.S.A. 48, 2013–2018.

Gilson, E., Mueller, T., Sogo, J., Laroche, T., and Gasser, S. (1994). RAP1 stimulates single- to double-stranded association of yeast telomeric DNA: implications for telomere—telomere interactions. Nucleic Acids Res. 22, 5310–5320.

Gottschling, D. E., and Zakian, V. A. (1986). Telomere proteins: specific recognition and protection of the natural termini of Oxytricha macronuclear DNA. Cell 47, 195–205.

Greider, C. W. (1995). Telomerase biochemistry and regulation. In Telomeres. vol. Monograph 29, E. H. Blackburn, and C. W. Greider, eds. (Cold Spring Harbor, N.Y.: Cold Spring Harbor Laboratory Press), pp. 35–68.

Greider, C. W., Blackburn, E. H. (1985). Identification of a specific telomere terminal transferase activity in Tetrahymena extracts. Cell 43, 405–413.

Gualberto, A., Patrick, R. M., and Walsh, K. (1992). Nucleic acid specificity of a vertebrate telomere-binding protein: evidence for G:G base pair recognition at the core binding site. Genes & Development 6, 815–824.

Hardin, C. C., Henderson, E., Watson, T., and Prosser, J. K. (1991). Monovalent cation-induced structural transitions in telomeric DNAs: G-DNA folding intermediates. Biochemistry 30, 4460–4472.

Harrington, J. J., and Lieber, M. R. (1994). Functional domains within FEN-1 and RAD2 define a family of structure-specific endonucleases: implications for nucleotide excision repair. Genes & Development 8, 1344–1355.

Henderson, E. R., and Blackburn, E. H. (1989). An overhanging 3' terminus is a conserved feature of telomeres. Mol. Cell. Biol. 9, 345–348.

Henikoff, S., and Eghtedarzadeh, M. K. (1987). Conserved arrangement of nested genes at the Drosophila Gart locus. Genetics 117, 711–725.

Hobza, P., and Sandorfy, C. (1987). Nonempirical calculations on all the 29 possible DNA base pairs. J. Am. Chem. Soc. 109, 1302–1307.

Huang, K. N., and Symington, L. (1993). A 5'-3' exonuclease from Saccharomyces cerevisiae is required for in vitro recombination between linear DNA molecules with overlapping homology. Mol. Cell. Biol. 13, 3125–3134.

Huberman, J. A., Spotila, L. D., Nawotka, K. A., El-Assouli, S. M., and Davis, L. R. (1987). The in vivo replication origin of the yeast 2 μm plasmid. Cell 51, 473–481.

Johnston, R. F., Pickett, S. C., and Barker, D. L. (1990). Autoradiography using storage phosphor technology, Eletrophoresis 11, 355–360.

Kang, C. H., Zhang, X., Ratliff, R., Moyzis, R., and Rich, A., (1992). Crystal structure of four-stranded Oxytricha telomeric DNA. Nature 356, 126–131.

Kerr, C., and Sadowski, P. D. (1972). Gene6 exonuclease of bacteriophage T7. II Mechanism of the reaction. J. Biol. Chem. 247, 311–318.

Klobutcher, L. A., Swanton, M. T., Donini, P., and Prescott, D. M. (1981). All gene-sized DNA molecules in four species of hypotrichs have the same terminal sequence and an unusual 3' terminus. Proc. Natl. Acad. Sci. U.S.A. 78, 3015–3019.

Kohwi, Y., and Kohwi-Shigematsu, T. (1988). Magnesium ion-dependent triple-helix formed by homopurine-homopyrimidine sequences in supercoiled plasmid DNA. Proc. Natl. Acad. Sci. U.S.A. 85, 3781–3785.

Lin, J. J., and Zakian, V. A. (1995). An in vitro assay for Saccharomyces telomerase requires EST1. Cell 81, 1127–1135.

Lingner, J., Cooper, J. P., and Cech, T. R. (1995). Telomerase and DNA end replication: no longer a lagging strand problem? Science 269, 1533–1534.

Lundblad, V., and Blackburn, E. H. (1993). An alternative pathway for yeast telomere maintenance rescues est1$^-$ senescence. Cell 73, 347–360.

Lundblad, V., and Szostak, J. W. (1989). A mutant with a defect in telomere elongation leads to senescence in yeast. Cell 57, 633–643.

McCarroll, R. M., and Fangman, W. L. (1988). Time of replication of yeast centromeres and telomeres. Cell 54, 505–513.

McClintock, B. (1939). The behavior in successive nuclear divisions of a chromosome broken at meiosis. Proc. Natl. Acad. Sci. U.S.A. 25, 405–416.

McClintock, B. (1941). The stability of broken ends of chromosomes in Zea mays. Genetics 26, 234–282.

McEachern, M. J., and Blackburn, E. H. (1995). Runaway telomere elongation caused by telomerase RNA gene mutations. Nature 376, 403–409.

Newlon, C. S. (1988). Yeast chromosome replication and segregation. Microbiol. Rev. 52, 568–601.

Olovnikov, A. M. (1973). A theory of marginotomy. J. Theor. Biol. 41, 181–190.

Pluta, A. F., and Zakian, V. A. (1989). Recombination occurs during telomere formation in yeast. Nature 337, 429–433.

Pluta, A. F., Kaine, B. P., and Spear, B. B. (1982). The terminal organization of macronuclear DNA in Oxytricha fallax. Nucleic Acids Res. 10, 8145–8154.

Price, C. M. (1990). Telomere structure in Euplotes crassus: characterization of DNA-protein interactions and isolation of a telomere-binding protein. Mol. Cell. Biol. 10, 3421–3431.

Runge, K. W., and Zakian, V. A. (1989). Introduction of extra telomeric DNA sequences into Saccharomyces cerevisiae results in telomere elongation. Mol. Cell. Biol. 9, 1488–1497.

Sadowski, P. D. (1985). Role of nucleases in genetic recombination. In Nucleases, S. M. Linn, and R. J. Roberts, eds. (Cold Spring Harbor, N.Y.: Cold Spring Harbor Laboratory Press), pp. 23–40.

Sandell, L. S., and Zakian, V. A. (1993). Loss of a yeast telomere: arrest, recovery, and chromosome loss. Cell 75, 729–739.

Scaria, P. V., Shire, S. C., and Shafer, R. H. (1992). Quadruplex structure of $d(G_3T_4G_3)$ stabilized by $K^+$ or $Na^+$ is an asymmetric hairpin dimer. Proc. Natl. Acad. Sci. U.S.A. 89, 10336–10340.

Schiestl, R. H., and Gietz, R. D. (1989). High efficiency transformation of intact yeast cells using single stranded nucleic acids as a carrier. Current Genetics 16, 339–346.

Sen, D., and Gilbert, W. (1988). Formation of parallel four-stranded complexes by guanine-rich motifs in DNA and its implications for meiosis. Nature 334, 364–366.

Sen, D., and Gilbert, W. (1990). A sodium-potassium switch in the formation of four-stranded G4-DNA. Nature 344, 410–414.

Sikorski, R. S., and Hieter, P. (1989). A system of shuttle vectors and yeast host strains designed for efficient manipulation of DNA in Saccharomyces cerevisiae. Genetics 122, 19–27.

Singer, M. S., and Gottschling, D. E. (1994). TLC1: Template RNA component of Saccharomyces cerevisiae telomerase. Science 266, 404–409.

Smith, F. W., and Feigon, J. (1992). Quadruplex structure of Oxytricha telomeric DNA oligonucleotides. Nature 356, 164–168.

Sommerville, J., and Scheer, U., eds. (1987). Electron Microscopy in molecular biology: a practical approach. (Oxford: IRL).

Stinchcomb, D. T., Thomas, M., Kelly, J., Selker, E., and Davis, R. W. (1980). Eukaryotic DNA segments capable of autonomous replication in yeast. Proc. Natl. Acad. Sci. U.S.A. 77, 4559–4563.

Sun, H., Treco, D., and Szostak, J. W. (1991). Extensive 3'-overhanging, single-stranded DNA associated with the meiosis-specific double-strand breaks at the ARG4 recombination initiation site. Cell 64, 1155–1161.

Sundquist, W. I. (1990). The structure of telomeric DNA. In Nucleic Acids and Molecular Biology, vol. 5, D. M. J. Lilley, and F. Eckstein, eds. (Heidelberg: Springer), pp. 1–24.

Sundquist, W. I. (1993). Conducting the G-quartet. Current Biology 3, 893–895.

Sundquist, W. I., and Klug, A. (1989). Telomeric DNA dimerizes by formation of guanine tetrads between hairpin loops. Nature 342, 825–829.

Sutcliffe, J. G. (1978). pBR322 restriction map marked from the DNA sequence: accurate DNA file markers up to 4361 nucleotide pairs long. Nucleic Acids Res. 5, 2721–2728.

Voloshin, O. N., Veselkov, A. G., Belotserkovskii, B. P., Danilevskaya, O. N., Pavlova, M. N., Dobrynin, V., and Frank-Kamenetskii, M. D. (1992). An eclectic DNA structure adopted by human telomere sequence under superhelical stress and low pH. J. Biomol. Struct. Dyn. 9, 643–652.

Wahl, G. M., Meinkoth, J. L., and Kimmel, A. L. (1987). Northern and Southern blots. Methods Enzymol. 152, 572–581.

Wang, S. -S., and Zakian, V. A. (1990). Telomere—telomere recombination provides an express pathway for telomere acquisition. Nature 345, 456–458.

Watson, J. D. (1972). Origin of concatemeric DNA. Nature (New Biology) 239, 197–201.

Wellinger, R. J., Zakian, V. A. (1989). Lack of positional requirements for autonomously replicating sequence elements on artificial yeast chromosomes. Proc. Natl. Acad. Sci. U.S.A. 86, 973–977.

Wellinger, R. J., Wolf, A. J., and Zakian, V. A. (1992). Use of non-denaturing Southern hybridization and two dimensional agarose gels to detect putative intermediates in telomere replication in *Saccharomyces cerevisiae*. Chromosoma 102, S150–S156.

Wellinger, R. J., Wolf, A. J., and Zakian, V. A. (1993a). The acquisition and association of $TG_{1-3}$ single-strand tails during replication of Saccharomyces telomeres. In Chromosome Segregation and Aneuploidy, vol. H 72, B. Vig, ed. (Berlin: Springer Verlag), pp. 133–141.

Wellinger, R. J., Wolf, A. J., and Zakian, V. A. (1993b). Origin activation and formation of single strand $TG_{1-3}$ tails occur sequentially in late S-phase on a yeast linear plasmid. Mol. Cell. Biol. 13, 4057–4065.

Wellinger, R. J., Wolf, A. J., and Zakian, V. A. (1993c). *Saccharomyces telomeres* acquire single-strand $TG_{1-3}$ tails late in S-phase. Cell 72, 51–60.

White, C. I., and Haber, J. E. (1990). Intermediates of recombination during mating type switching in *Saccharomyces cerevisiae*. Embo J. 9, 633–670.

Wiley, E. A., and Zakian, V. A. (1995). Extra telomeres, but not internal tracts of telomeric DNA, reduce transcriptional repression at *Saccharomyces telomeres*. Genetics 139, 67–79.

Williamson, J. R., Raghuraman, M. K., and Cech, T. R. (1989). Monovalent cation-induced structure of telomeric DNA: The G-Quartet model. Cell 59, 871–880.

Zakian, V. A. (1995). Telomeres: Beginning to understand the end. Science 270, 1601–1607.

Zakian, V. A., and Scott, J. F. (1982). Construction, replication and chromatin structure of TRP1 RI circle, a multiple-copy synthetic plasmid derived from *Saccharomyces cerevisiae* chromosomal DNA. Molec. Cell. Biol. 2, 221–232.

All publications and patent documents cited in this application are incorporated by reference in their entirety for all purposes to the same extent as if each individual publication or patent document were so individually denoted.

Tables.

TABLE 1

Fraction of in vivo synthesized molecules with end-to-end interactions.

| | |
|---|---|
| A) As measured in a two-dimensional gel (circular form, fraction of total) | 1.9% |
| B) As measured in a one-dimensional gel (junction fragment, fraction of total) | 2.1% |

Table 1. The fraction of YLpFAT10 molecules that had end-to-end interactions in the two-dimensional gel system (circular form of the plasmid (CFP), see FIG. 5B and Wellinger et al., 1993c) and the fraction of molecules with end-to-end interactions as indicated by a restriction fragment joining the two ends and detected in the one-dimensional gel (see FIG. 5A, and Wellinger et al., 1993c). The signals from two independent experiments were quantified by a PhosphorImager and expressed as % of the total amount of YLpFAT10 molecules.

What is claimed is:

1. A method for detecting 5'-3' exonuclease activity in a sample comprising the steps of:

contacting the sample with a substrate linear double-stranded nucleic acid molecule wherein at least one end of such molecule does not have a 3' overhang; and determining whether a resulting linear nucleic acid molecule has 3' overhangs at both ends, whereby the presence of 3' overhangs at both ends of the resulting nucleic acid molecule indicates the presence of 5'-3' exonuclease activity in the sample.

2. The method of claim 1 wherein the sample comprises a cell transfected with the linear nucleic acid molecule.

3. The method of claim 2 wherein the cell is a yeast.

4. The method of claim 2 wherein the cell is mammalian cell.

5. The method of claim 2 wherein the 3' overhang on the first end comprised $TG_{1-3}$ repeats and the cell is a yeast cell or a mammalian cell.

6. The method of claim 2 wherein the cell lacks telomerase activity and the cell is a yeast cell or a mammalian cell.

7. The method of claim 1 wherein the 5'-3' exonuclease is FEN-1 or RAD27.

8. The method of claim 1 wherein the 5'-3' exonuclease is a mammalian homologue of FEN-1 or RAD27.

9. The method of claim 1 wherein the 5'-3' exonuclease is a human homologue of FEN-1 or RAD27.

10. The method according to claim 1, wherein the sample contains a known quantity of a 5'-3' exonuclease and the method additionally comprises the steps of:

determining the amount of 5'-3' exonuclease activity in the sample after contact with a compound; and comparing the amount of the 5'-3' exonuclease activity in the sample with a standard activity for the same quantity of the exonuclease, whereby a difference between the amount of activity in the sample and the standard activity indicates that the compound modulates the activity of the 5'-3' exonuclease.

11. The method according to claim 10, wherein the sample contains an enzyme which regulates a 5'-3' exonuclease, and the method additionally comprises the steps of:

comparing the amount of 5'-3' exonuclease activity in the sample before and after contact with a compound, whereby a difference between the amount of activity in the sample before and after contact with the compound, beyond that which can be attributed to the effect of the compound directly on the exonuclease, indicates that the compound modulates the activity of the enzyme.

12. A method for detecting 5'-3' exonuclease activity in a sample comprising the steps of:

contacting the sample with a substrate linear double-stranded nucleic acid molecule, wherein at least one end of such molecule does not have a 3' overhang; and determining whether a resulting nucleic acid molecule has 3' overhangs at both ends based on whether the resulting nucleic acid molecule undergoes end-to-end interactions, whereby the presence of 3' overhangs at both ends of the resulting linear nucleic acid molecule indicates the presence of 5'-3' exonuclease activity in the sample.

13. The method of claim 12 wherein one end of the substrate linear nucleic acid molecule has a 3' overhang and the other end has a blunt end.

14. The method of claim 12 wherein the resulting linear nucleic acid molecule is determined to undergo end-to-end interactions if the resulting molecule circularizes.

15. The method of claim 12 wherein the resulting linear nucleic acid molecule is determined to undergo end-to-end interactions if the resulting molecule forms linear concatenations of at least three linear nucleic acid molecules.

16. The method of claim 15 wherein the step of determining whether both ends of the linear nucleic acid molecule have 3' overhangs comprises determining the length of the 3' overhangs in the linear nucleic acid molecule.

17. The method as in any of claims 1–16 wherein the 5'-3' exonuclease is involved in telomerase maintenance.

* * * * *

UNITED STATES PATENT AND TRADEMARK OFFICE
CERTIFICATE OF CORRECTION

PATENT NO. : 6,025,135
DATED : February 15, 2000
INVENTOR(S) : Raymund J. Wellinger, *et al.*

It is certified that error appears in the above-identified patent and that said Letters Patent is hereby corrected as shown below:

In Column 19, line 12, after "cell is" add --a--.

In Column 19, line 15, delete "comprised" and insert therefor --comprises--.

Signed and Sealed this

Twenty-fourth Day of April, 2001

Attest:

NICHOLAS P. GODICI

Attesting Officer

Acting Director of the United States Patent and Trademark Office

UNITED STATES PATENT AND TRADEMARK OFFICE
CERTIFICATE OF CORRECTION

PATENT NO.   : 6,025,135
DATED        : February 15, 2000
INVENTOR(S)  : Raymund J. Wellinger et al.

It is certified that error appears in the above-identified patent and that said Letters Patent is hereby corrected as shown below:

<u>Column 19,</u>
Line 12, after "cell is" add -- a --.
Line 15, delete "comprised" and insert therefor -- comprises --.

Signed and Sealed this

Ninth Day of July, 2002

Attest:

JAMES E. ROGAN
*Attesting Officer*   *Director of the United States Patent and Trademark Office*